US00PP18749P2

(12) United States Plant Patent
Utecht

(10) Patent No.: US PP18,749 P2
(45) Date of Patent: Apr. 22, 2008

(54) ***PELARGONIUM* PLANT NAMED 'FISPRIT'**

(50) Latin Name: *Pelargonium peltatum*
Varietal Denomination: Fisprit

(75) Inventor: Angelika Utecht, Montabur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 11/506,133

(22) Filed: Aug. 17, 2006

(51) Int. Cl.
*A01H 5/00* (2006.01)

(52) U.S. Cl. ..... Plt./332

(58) Field of Classification Search ..... Plt./332
See application file for complete search history.

(56) References Cited

PUBLICATIONS

UPOV–ROM GTITM, Plant Variety Database, Jan. 2007, GTI Jouve Retrieval Software, Citation for Pelargonium 'Fisprit'and 'Fiv 269', 2 pages.*
Flora–Nova Pflanzen GmbH [retreived on Jul. 30, 2007]. Retreived from the Internet: <http://www.top500.de/details/475/flora–nova_pflanzen_gmbh_germany.php>2 pages.*

* cited by examiner

*Primary Examiner*—Kent Bell
*Assistant Examiner*—June Hwu
(74) *Attorney, Agent, or Firm*—Jondle & Associates, P.C.

(57) ABSTRACT

A new cultivar of *pelargonium* particularly characterized by having large, light-pink, double flowers with reddish markings, floriferous, medium-sized and semi-spherically shaped umbels, medium-green, glossy foliage with weak to distinct zonation, a bushy, slightly trailing, medium-sized plant habit, good branching ability and a mid-season flowering response, is disclosed.

1 Drawing Sheet

Genus and species: *Pelargonium peltatum.*
Variety denomination: 'Fisprit'.

BACKGROUND OF THE NEW PLANT

The present invention comprises a new and distinct cultivar of *pelargonium,* botanically known as *Pelargonium peltatum,* and hereinafter referred to by the cultivar name 'Fisprit'. The new cultivar is a product of a planned breeding program which had the objective of creating new ivy geraniums in a variety of colors, having double flowers, zoned foliage and medium-sized and well-branched plant habits. 'Fisprit' was discovered as a seedling resulting from the cross of the female parent '97-2388-9' (unpatented), a proprietary *pelargonium* plant having white flowers and the male parent '98-3122-5' (unpatented), a proprietary *pelargonium* plant having light-pink flowers.

The new cultivar was created in 2001 in Hillscheid, Germany and has been asexually reproduced repeatedly by vegetative cuttings in Galdar, Gran Canaria, Spain, and Hillscheid, Germany over a four-year period. It has been found to retain its distinctive characteristics through successive asexual propagations. 'Fisprit' reproduces true to type in successive generations of asexual reproduction.

Plant Breeder's Rights for this cultivar were applied for in Germany on Apr. 4, 2005 and Canada on Apr. 20, 2005.

SUMMARY OF THE INVENTION

The following are the most outstanding and distinguishing characteristics of this new cultivar when grown under normal horticultural practices in Hillscheid, Germany.

1. Large, light-pink, double flowers with reddish markings;

2. Floriferous with medium-sized, semi-spherically shaped umbels well above the foliage;
3. Medium-green, glossy foliage with weak to distinct zonation;
4. A medium-sized, bushy and slightly trailing plant habit;
5. Good branching ability; and
6. A mid-season flowering response.

DESCRIPTION OF THE PHOTOGRAPH

This new *pelargonium* plant is illustrated by the accompanying photograph which shows overall plant habit including inflorescences, buds, and foliage of the plant; the colors shown are as true as can be reasonably obtained by conventional photographic procedures. The photograph is of three 30-week-old plants in a hanging basket in early September and grown under greenhouse and outdoor conditions which approximate those generally used in commercial practice.

DESCRIPTION OF THE NEW CULTIVAR

The following detailed description sets forth the distinctive characteristics of 'Fisprit'. The data which define these characteristics were collected from asexual reproductions carried out in Hillscheid, Germany. The plant history was taken on 15-week old plants, pinched once, in 12-cm pots in a greenhouse during late May. Color readings were taken under natural light in mid-May from flowers grown in the greenhouse. Color references are primarily to the R.H.S. Colour Chart of The Royal Horticultural Society of London (R.H.S.) (2001).

DETAILED BOTANICAL DESCRIPTION

Classification:

*Family.*—Geraniaceae.

*Botanical.*—*Pelargonium peltatum.*

*Common name.*—Ivy geranium.

Parentage:

*Female parent.*—'97-2388-9' a proprietary *pelargonium* plant having white flowers (unpatented).

*Male parent.*—'98-3122-5', a proprietary *pelargonium* plant having light-pink flowers (unpatented).

Plant:

*Form.*—Shrub, self-branching, initially spreading, later trailing.

*Branching habit.*—12 to 14 branches per plant.

*Height* (*measured from base of the stem to the tips of the branches, excluding the inflorescence*).—2.5 cm.

*Width* (*plant diameter*).—32 cm.

*Plant spread at end of summer* (*about 30 weeks old*).—65 cm.

*Time to produce a finished flowering plant.*—About 12 weeks after planting rooted cuttings in Hillscheid, Germany.

*Outdoor plant performance.*—Plants continuously flower; a count in late summer of 30-week old plants in Hillscheid, Germany produced about 30 inflorescences per plant.

Leaves:

*Arrangement.*—Initially alternate, opposite at flowering stems.

*Immature leaf color.*—Medium-green. Upper surface: RHS 137D. Lower surface: RHS 143C.

*Mature leaf color.*—Upper surface: RHS 137C (medium-green). Lower surface: RHS 143C.

*Zonation color.*—RHS 166A (brown) with a weak to medium distinctness.

*Zonation diameter.*—Inner diameter of ring: 1.5 cm. Band or belt of zonation: 1.2 cm.

*Size.*—Length: 3.2 cm to 3.7 cm. Width: 7.5 cm.

*Shape.*—Ivy-shaped with 5 lobes and with the lowest lobes overlapping.

*Apex.*—Rounded with lobes.

*Base.*—Cordate.

*Margin.*—Entire.

*Texture.*—Upper surface: Leathery with smooth upper surface, glabrous and short hairs along with the edge of the leaves. Lower surface: Smooth part from the protruding veins, covered with fine pubescence.

*Petioles.*—Color: RHS 143C (light-green). Length: 3 cm to 5 cm. Diameter: 0.2 cm to 0.3 cm. Texture: Covered with short pubescence.

Stems:

*Stem color.*—RHS 143C (green).

*Anthocyanin.*—RHS 180B (small amount near the nodes).

*Length.*—19 cm to 27 cm.

*Internode length.*—1.5 cm to 2.0 cm.

*Texture.*—Appears smooth but with short pubescence.

Inflorescence bud: (just before petals unfold).

*Shape.*—Elliptical.

*Size.*—Length: 1.5 cm. Width: 0.9 cm to 1.2 cm.

*Color of sepals.*—RHS 143B to RHS 143C (light-green).

*Color of petals.*—RHS 65B to RHS 65C (light-pink).

Inflorescence:

*Inflorescence type.*—An umbel composed of 7 to 15 flowers.

*Umbel.*—Shape: Semi-spherical. Diameter: 8.9 cm. Height (depth): 4.9 cm to 5.1 cm.

*Lastingness of umbel on the plant.*—About 14 to 16 days.

*Peduncle.*—Color: RHS 143B to RHS 143C (light-green). Length: 14.3 cm. Diameter: 0.3 cm. Texture: With sparse pubescence.

*Pedicel.*—Color: Upper part: RHS 181B (brown). Lower part: RHS 143C (light-green). Length: 2.1 cm, usually with a spur. Diameter: 0.15 cm. Texture: Weak pubescence.

Corolla:

*Shape of corolla.*—Large, shallow cup-shaped, sometimes with a gap between the upper and lower petals.

*Form.*—Double.

*Diameter.*—5.7 cm.

*Depth.*—1.5 cm.

*Number of petals.*—14 to 16.

*Petaloids.*—Shape: Variable, narrower and shorter than the petals, often twisted Number: 2 to 5 Color: RHS 73C to RHS 75B

*Lastingness of individual flowers on plant.*—8 days at 18° C.

*Fragrance.*—None.

Petals:

*Shape.*—Obovate.

*Apex.*—Rounded.

*Base.*—Acute.

*Margin.*—Entire.

*Texture.*—Upper surface: Smooth, slightly glossy. Lower surface: Glabrous.

*Upper petals.*—Length: 3.3 cm to 3.6 cm. Width: 2.0 cm to 2.2 cm. Color: Upper surface: From RHS 65B to RHS 65C or RHS 75B (light bluish-pink). Lower surface: RHS 75C. Markings: Distinct RHS N57B (red-purple) spots and RHS 67A veins near the base.

*Lower petals.*—Length: 2.8 cm to 2.9 cm. Width: 2.0 cm to 2.2 cm. Color: Upper surface: From RHS 77D to RHS 75B. Lower surface: RHS 75C or between RHS 73C and RHS 73D. Markings: Absent.

Sepals:

*Number.*—5 to 6.

*Color.*—RHS 143C (light-green) for both surfaces with an RHS 179A (brown) spot near the base.

*Length.*—1.2 cm to 1.3 cm.

*Width.*—Largest upper sepal: 0.6 cm. Other sepals: 0.3 cm to 0.4 cm.

*Shape.*—Lanceolate.

*Apex.*—Acute.

*Base.*—Fused.

*Margin.*—Entire.

*Texture.*—Upper surface: Glabrous. Lower surface: Dense, short pubescence with some long hairs.

Reproductive organs:

*Androecium.*—Number of anthers: 2 to 5. Filament length: 0.8 cm to 1.0 cm. Filament color: RHS 155D (white) to RHS 75C at the upper end. Pollen color: RHS 25A to RHS 26A (orange). Pollen amount: Moderate.

*Gynoecium.*—Pistil: Number: 1. Length: 0.8 cm to 0.9 cm. Stigma color: RHS 58D (purple-pink). Stigma shape: Often to 6-to-7 lobed. Style color: RHS 62D (pale-pink). Style length: 0.3 cm. Style shape: Filiform (filament-like) with the lobes of the stigma at right angles or decurrent.

Fruit and seed set: No seed set observed.

Disease and insect resistance: No particular resistance or susceptibility has been observed.

COMPARISON WITH PARENTAL AND COMMERCIAL CULTIVARS

'Fisprit' differs from the female parent '97-2388-9' (unpatented) by having light-pink, double flowers, while '97-2388-9' has white, single-type flowers.

'Fisprit' differs from the male parent '98-3122-5' (unpatented) by having stronger leaf zonation, better branching and better propagation characteristics such as quick rooting of cuttings and usually has green shoot tips, while '98-3122-5' is slower to root and has a tendency to develop nearly white shoot tips under hot conditions in the spring.

'Fisprit' differs from the commercial variety 'Fiswipink' (U.S. Plant Pat. No. 16,686) by having a lighter pink but more bluish-pink overall flower color than 'Fiswipink'. In addition, 'Fisprit' has a smaller ring of leaf zonation than 'Fiswipink'.

'Fisprit' differs from the commercial variety 'Fisam' (U.S. Plant Pat. No. 8,327) by having light-pink flowers, while 'Fisam' has light-violet flowers. In addition, 'Fisprit' has a tighter plant habit and a weaker leaf zonation than 'Fisam'.

I claim:

1. A new and distinct cultivar of *pelargonium* plant as shown and described herein.

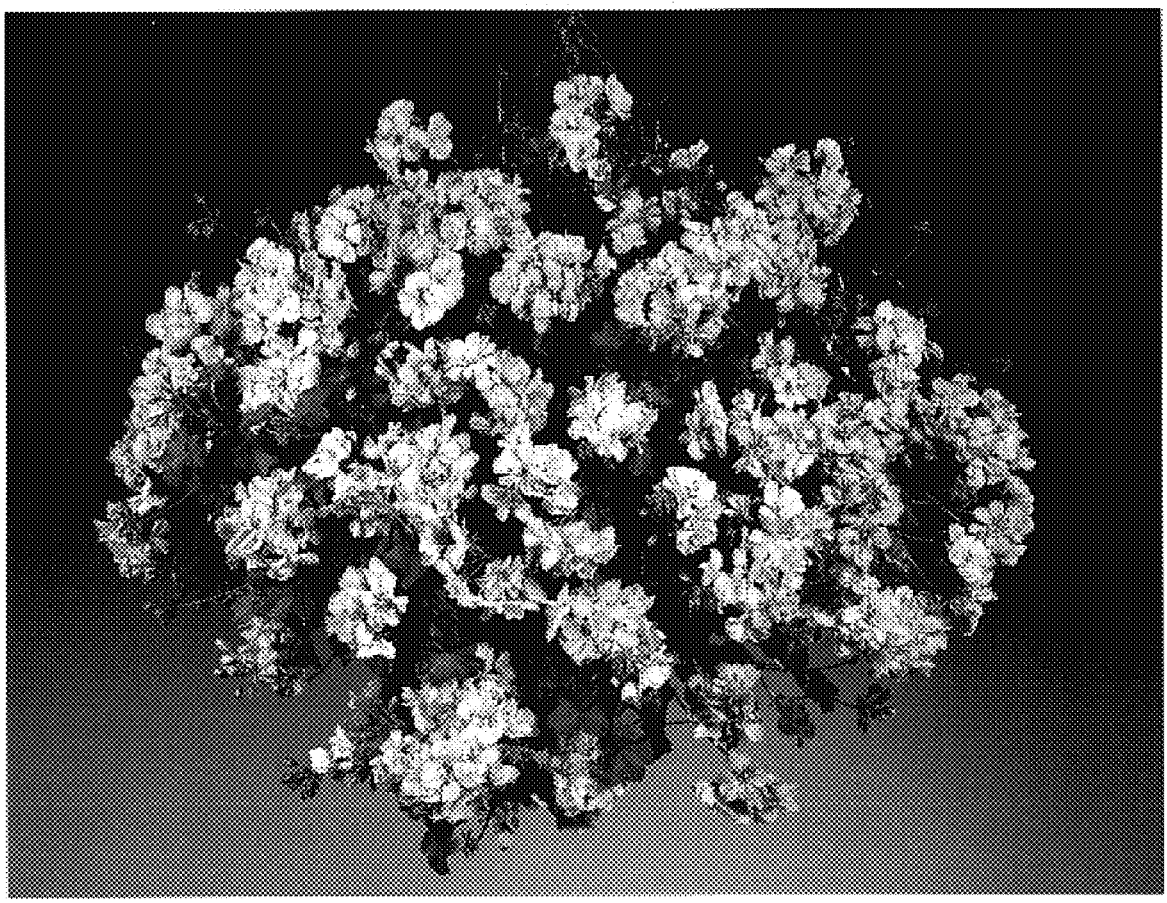

* * * * *